United States Patent [19]

Klosa

[11] 4,416,878
[45] Nov. 22, 1983

[54] [8-(DIALKYLAMINO ALKOXY)-CAFFEINE]-PLATINUM COMPLEX COMPOUNDS AND PHARMACEUTICAL PRODUCTS CONTAINING THE SAME

[76] Inventor: Josef Klosa, Jänickestrasse 13, D-1000 Berlin, Fed. Rep. of Germany

[21] Appl. No.: 327,712

[22] Filed: Dec. 4, 1981

[30] Foreign Application Priority Data

Dec. 11, 1980 [DE] Fed. Rep. of Germany ....... 3046927

[51] Int. Cl.³ .................. A61K 31/515; C07D 473/12
[52] U.S. Cl. .................................... 424/245; 544/225; 424/251
[58] Field of Search ................. 544/225; 424/251, 245

[56] References Cited

U.S. PATENT DOCUMENTS 3,794,648  2/1974  Hammond et al. ................. 544/225
4,080,324  3/1978  Hoeschelk ........................... 544/225

FOREIGN PATENT DOCUMENTS 2445418  4/1976  Fed. Rep. of Germany ...... 544/225
2729080  1/1979  Fed. Rep. of Germany ...... 544/225
 142293  6/1980  German Democratic Rep. .

OTHER PUBLICATIONS

Melnik, "J. Inorg. Chem." vol. 43, No. 11, 1981, pp. 3035–3038.
Rosenberg, et al. "Nature," vol. 222, 4/26/69, pp. 385–386, Cleare, "Coordination Chemistry Reviews," vol. 12, 1974, pp. 349–405.

Primary Examiner—Donald G. Daus
Assistant Examiner—James H. Turnipseed
Attorney, Agent, or Firm—Cushman, Darby & Cushman

[57] ABSTRACT

New [8-(dialkylamino alkoxy)-caffeine]-platinum complex compounds of the general formula

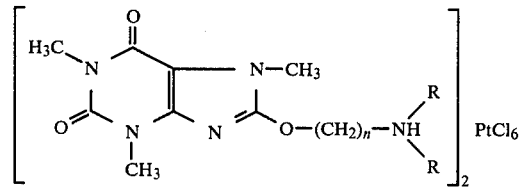

are prepared from 8-(dialkylamino alkoxy)-caffeine and hexachloro platinic acid. The complex compounds are nonpoisonous, stable and infinitely durable. In pharmacological test series distinct cytostatic activity of the complex compounds is observed and they are suitable for use as active components in pharmaceutical products.

2 Claims, No Drawings

[8-(DIALKYLAMINO ALKOXY)-CAFFEINE]-PLATINUM COMPLEX COMPOUNDS AND PHARMACEUTICAL PRODUCTS CONTAINING THE SAME

This invention relates to [8-(dialkylamino alkoxy)-caffeine]platinum complex compounds; the invention also relates to a process of preparing the above-mentioned compounds as well as their use in pharmaceutical products for application in human and veterinary medicine.

The cytostatic activity of certain platinum coordination compounds is well known (Rosenberg et al., Nature 222, 385 to 386 (1969)). Several classes of coordination complexes have since been studied for anti-tumor activity, see M. G. Cleare, Coordination Chemistry Reviews 12, 349 to 405 (1974) and A. J. Thomson, Nachr. Chem. Techn. Lab. 25, 20 to 23 (1977).

In the course of these efforts cis-dichloro diammine platinum (DDP) was found to be a most promising anti-cancer remedy (DD-PS No. 142 293). The said composition is an inorganic complex compound, consisting of a central platinum atom surrounded by two chlorine atoms and two ammonia groups in cis-position.

Disadvantageously this composition is highly poisonous; for this reason it is very difficult to handle and for the use of it in medical treatment heavy precautions have to be taken. Also the attempt to overcome the disadvantages of DDP by preparing an organophosphate complex, as described in DE-OS No. 30 08 661, led to only small success, since it is already very difficult to handle the highly poisonous starting material.

It is further known from literature that certain caffeine derivatives, for instance 8-(dialkylamino alkoxy)-caffeine develop some cancerostatic activity, see J. Klosa, J. prakt. Chemie 6, 8 to 13 (1958); ibid. 18, 117 (1962); A. M. Rusanow et al., Vopr. Radiobiol. Deistvija Tsitostatich Prep. 8, 80 (1977) [C. A. 91, 49393y (1979)].

Surprisingly 4-valent platinum in caffeine complex compounds, which are well compatible, develop convincing anti-tumor activity already in amounts of 10 to 50 mg/kg bodyweight when tested on mice. As a result of the wide range of previous experience no anti-tumor activity of 4-valent platinum could be expected.

By means of the [8-(di-alkylamino alkoxy)-caffeine]-platinum complex compounds of this invention a remedy especially for treatment of tumors is provided which is extraordinarily stable and at the same time does not cause any skin irritation or etching, so that the extensive precautions necessary when applying DDP or DDP-containing products, are not necessary.

In practicing the present invention equimolar amounts of an alcoholic solution of 8-(dialkylamino alkoxy)-caffeine of the general formula

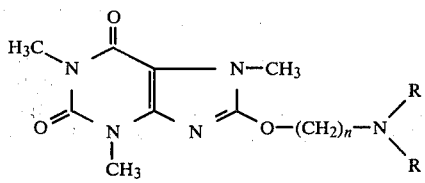

wherein n is 2 or 3 and R is an alkyl group with 1 to 3 carbon atoms, the chain of carbon atoms being straight or branched, and an alcoholic solution of hexachloro platinic acid are mixed together, by which process a new complex compound of the general formula

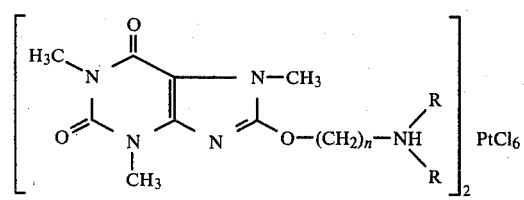

is formed either immediately or within a few hours depending on its constitution, which cristallizes in characteristically golden-yellow coloured crystals and which is easily recrystallized from an aqueous alcoholic solution. The new complex compounds are able to bind additional water as crystal water. They are stable and unlimitedly durable.

The complex compounds of this invention show excellent healing activity when used for treatment of experimentally effected animal cancer, i.e. ascites tumors of mice, while the starting material hexachloro platinic acid is without any anti-tumor activity. Cosidering the non-toxicity and thus the possibility of being handled without precaution, the stableness and infinite durability of the complex compounds of this invention, an important technical progress becomes evident in comparison with other platinum containing drugs for tumor treatment.

The complex compounds of this invention may be formulated according to conventional methods for preparation of pharmaceutical products, to provide tablets, pills, solutions or syrups especially for treatment of malignant tumors, but there is no limitation proposed with respect to the way and the field of application of the pharmaceutical products of this invention.

The following examples illustrate the invention but are in now way intended to limit the same.

EXAMPLE 1

Preparation of di-[8-(2-diisopropylamino ethoxy)-caffeine]hexachloroplatinate 10 ml of diisopropylamino ethanol were dissolved in 50 ml of toluene. To this solution 1.2 g of sliced sodium was added. The mixture was heated to about 50° to 60° C. for about 6 to 8 hours. During this time all of the sodium was dissolved to form the sodium salt of the diisopropylamino ethanol. Thereafter 11 g of well dried 8-chlorocaffeine were added batchwise within 20 minutes while stirring; subsequently the mixture was heated to about 40° to 50° C. on a water bath for about 20 minutes and thereafter left alone for about 5 hours. After that time the composition was separated from the sodium chloride by suction and the toluene was evaporated while the filtrate was kept under vacuum on a water bath. The oily residue was treated with a small amount of methanol so that colourless crystals were formed. The thus prepared substance had a Fp. of about 72° to 74° C., it was re-crystallized by dissolving it in aqueous methanol; Fp. 90° to 92° C., yield 12 g.

6.6 g of the thus prepared 8-(diisopropylamino ethoxy)caffeine were dissolved in 20 ml methanol. To the waterclear solution 5.2 g of hexachloro platinic acid hexahydrate in 10 ml of methanol were added dropwise. Immediately golden-yellow coloured crystals were formed. To complete crystallization 20 ml of acetone were added, the mixture was allowed to stand for about 2 hours, subsequently it was sucked off, washed with acetone and dried on clay. The Fp. determination showed brown colouring from 190° C. and decomposition by formation of a black, tarry melt from about 218° to 220° C. After recrystallization from hot 60% ethanol and subsequent cooling golden-yellow bar-shaped crystals were obtained.

Analysis:

Fp. 190° C. brown colouring, 200° C. black, tarry melt (decomposition).

Yield: 9.5 g $(C_{16}H_{28}N_5O_3)_2PtCl_6$

Molecular weight: 1028,35
Calc. Pt 18,02%
Found: Pt 18,10%

EXAMPLE 2

Preparation of di-[8-(3-dimethylamino propopxy)-caffeine]hexachloroplatinate 6.6 g of 8-(3-dimethylamino propoxy)-caffeine, prepared according to J. Klosa (J.prakt. Chemie, 6, 8–13 (1958)), Fp. of about 58° to 60° C., were dissolved in 30 ml of methanol. To this solution 5.2 g of hexachloro platinic acid hexahydrate in 20 ml of methanol were added dropwise within 10 minutes at room temperature while stirring. A golden-yellow sandy precipitate was formed which was sucked off after 3 hours standing and was washed with acetone.

Analysis:

Fp. 180° to 182° C. (orange-coloured melt)

Yield: 10 g. The product contained 3 moles of water as water of hydration.

$(C_{13}H_{22}N_5O_3)_2PtCl_6 \cdot 3H_2O$

Calc.: Pt 18,54%.
Found: Pt 18,35%.

The new complex compound is water-soluble.

Following the same procedure as described above di-[8-(2-diethylaminoethoxy)-caffeine]hexachloroplatinate was prepared from 8-(2-diethylaminoethoxy)-caffeine and hexachloroplatinic acid, Fp. 194° and 196° C., yield about 80%.

EXAMPLE 3

Preparation of pharmaceutical formulations (a) Capsules

The following components were mixed together and 100 mg of the mixture were filled into each capsule.

| | |
|---|---|
| Di-[8-(3-dimethylamino propoxy)-caffeine]-hexachloroplatinate according to example 2 | 30 mg |
| Lactose | 70 mg |

(b) Tablets

The following components were mixed, agglomerated on a compactor and subsequently granulated and pressed to tablets or pills:

| | |
|---|---|
| Di-[8-(3-dimethylamino propoxy)-caffeine]-hexachloroplatinate according to example 2 | 50 mg |
| Hydroxy ethyl cellulose | 30 mg |
| Polyvinyl pyrrolidine | 10 mg |
| Talcum | 6 mg |
| Magnesium stearate | 4 mg |
| | 100 mg |

(c) Ampuls

| Components: | |
|---|---|
| Di-[8-(3-dimethylamino propoxy)-caffeine]-hexachloroplatinate according to example 2 | 60 mg |
| Sodium chloride | 16 g |
| Redestilled water ad | 2000 g |

The caffeine platinate according to example 2 was dissolved in the freshly destilled water together with the sodium chloride. The solution was filtered and filled into 2-ml ampuls. After sealing the ampuls were sterilized for about 30 minutes at 120° C. in an autoclave.

EXAMPLE 4

Investigation of the cancero-static activity of di-[8-(3-dimethylamino propoxy)-caffeine]-hexachloroplatinate on mice and rats For treatment of Ehrlich tumors in the paw area of mice di-[8-(3-dimethylamino propoxy)-caffeine]-hexachloroplatinate was injected every second day for a total of 3 times in an amount of 50 mg/kg bodyweight. In 70% of all cases healing was observed within a few days.

In corresponding test series with the same dose applied as above described the development of Ehrlich ascites cells could be inhibited and in 15% of all cases healing was observed.

During additional investigations on sarkoma 180 of mice and Yoshida-sarkoma of rats (both in the ascites form) inhibition of growth was observed in all cases.

I claim:

1. Di-[8-(dialkylamino alkoxy)-caffeine]-hexachloroplatinates of the formula:

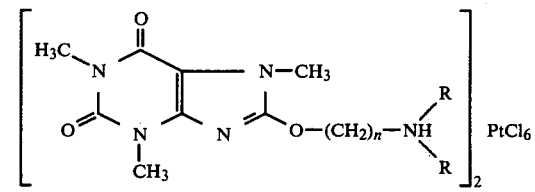

wherein n is 2 or 3 and R is a straight or branched alkyl having from 1 to 3 carbon atoms.

2. A pharmaceutical composition for the treatment of malignant tumors containing as the active ingredient a cytostatically effective amount of the compound of claim 1 together with a pharmaceutically acceptable carrier.

* * * * *